(12) United States Patent
Nguyen et al.

(10) Patent No.: US 8,658,140 B2
(45) Date of Patent: Feb. 25, 2014

(54) COMPOSITIONS AND METHODS FOR TREATING KERATINOUS SUBSTRATES

(75) Inventors: Nghi Van Nguyen, Edison, NJ (US); David W. Cannell, Plainfield, NJ (US); Sawa Hashimoto, Westfield, NJ (US); Cynthia Espino, Princeton, NJ (US)

(73) Assignee: L'Oreal, Paris (FR)

( * ) Notice: Subject to any disclaimer, the term of this patent is extended or adjusted under 35 U.S.C. 154(b) by 460 days.

(21) Appl. No.: 11/855,827

(22) Filed: Sep. 14, 2007

(65) Prior Publication Data

US 2009/0074683 A1    Mar. 19, 2009

(51) Int. Cl.
*A61K 8/00* (2006.01)
*A61K 8/18* (2006.01)

(52) U.S. Cl.
USPC ............................................ 424/59; 424/70.1

(58) Field of Classification Search
USPC ........................................ 424/59, 70.1, 70.21
See application file for complete search history.

(56) References Cited

U.S. PATENT DOCUMENTS

| | | | | |
|---|---|---|---|---|
| 3,590,122 A | * | 6/1971 | Hutchenson et al. | 424/70.19 |
| 3,689,424 A | | 9/1972 | Berg et al. | |
| 3,769,398 A | | 10/1973 | Hewitt | |
| 3,883,356 A | | 5/1975 | Syrovatka et al. | |
| 4,488,564 A | | 12/1984 | Grollier et al. | |
| 5,196,188 A | | 3/1993 | Potthoff-Karl et al. | |
| 5,360,581 A | * | 11/1994 | Rizvi et al. | 510/122 |
| 5,891,956 A | | 4/1999 | Smith et al. | |
| 5,897,870 A | | 4/1999 | Schehlmann et al. | |
| 5,951,718 A | | 9/1999 | Krutak et al. | |
| 6,139,853 A | | 10/2000 | Akram et al. | |
| 6,410,005 B1 | | 6/2002 | Galleguillos et al. | |
| 6,455,058 B1 | * | 9/2002 | Sun et al. | 424/401 |
| 6,468,515 B1 | * | 10/2002 | Uchiyama et al. | 424/70.27 |
| 6,548,051 B2 | | 4/2003 | Garnier et al. | |
| 6,589,517 B1 | | 7/2003 | McKelvey et al. | |
| 6,740,130 B2 | | 5/2004 | Sander et al. | |
| 7,083,655 B2 | | 8/2006 | Pratt et al. | |
| 7,094,262 B2 | | 8/2006 | Lagrange et al. | |
| 7,122,062 B2 | | 10/2006 | Yamashita et al. | |
| 7,141,079 B2 | | 11/2006 | Audousset et al. | |
| 2002/0034489 A1 | | 3/2002 | Wiegland et al. | |
| 2002/0085988 A1 | * | 7/2002 | Nambu | 424/70.19 |
| 2004/0063592 A1 | * | 4/2004 | Nguyen et al. | 510/124 |
| 2004/0234471 A1 | * | 11/2004 | Corbella et al. | 424/70.1 |
| 2006/0024255 A1 | | 2/2006 | Quadir et al. | |
| 2006/0078521 A1 | * | 4/2006 | Samain et al. | 424/70.11 |
| 2006/0286057 A1 | | 12/2006 | Cannell et al. | |
| 2007/0107635 A1 | * | 5/2007 | Soane et al. | 106/493 |
| 2007/0110690 A1 | | 5/2007 | Nguyen et al. | |

FOREIGN PATENT DOCUMENTS

| | | |
|---|---|---|
| EP | 0627217 A2 | 12/1994 |
| EP | 1787682 A1 | 5/2007 |
| EP | 1787686 A1 | 5/2007 |
| JP | 2003081781 A | 3/2003 |
| JP | 2005089372 A | 4/2005 |
| WO | 97/45510 A1 | 12/1997 |
| WO | 01/22928 A1 | 4/2001 |
| WO | WO-03033636 A1 | 4/2003 |

OTHER PUBLICATIONS

"Datasheet for SF96 350", Aug. 29, 2008, XP55042844, Retrieved from the Internet: URL: http://colonialchemicals.com/uploads/Products/Silicone_Fluid_SF_96-350/Silicone_Fluid_SF96-350_Tech.pdf [retrieved on Oct. 31, 2012], the whole document.
Extended European Search Report, EP Application No. 08253011.4, received on Nov. 12, 2012.

* cited by examiner

*Primary Examiner* — Brian-Yong Kwon
*Assistant Examiner* — Jennifer Berrios
(74) *Attorney, Agent, or Firm* — Novak Druce Connolly Bove + Quigg LLP

(57) ABSTRACT

The disclosure relates to compositions and methods of using the compositions to treat keratinous substrates. The compositions provide a water resistant and non-transferable protective barrier on the substrate. The compositions contain at least one polyamine, at least one acid, at least one water-insoluble ingredient, solvent and optionally at least one auxiliary ingredient. The methods for treating keratinous substrates involve contacting the keratinous substrates with the compositions of the disclosure.

14 Claims, No Drawings

COMPOSITIONS AND METHODS FOR TREATING KERATINOUS SUBSTRATES

TECHNICAL FIELD

The disclosure relates to compositions and methods for treating keratinous substrates. The compositions and methods provide a water resistant and non-transferable protective barrier on keratinous substrates imparting the substrates with improved properties.

BACKGROUND OF THE DISCLOSURE

When keratinous substrates are exposed to environmental conditions, the substrates can lose many of their desirable properties. For example, hair can lose its shine, it can become unmanageable, it can lose its color and it can become brittle. One method of maintaining these desirable properties is to provide a protective barrier on keratinous substrates like hair. For example, under low humidity conditions, hair can dry out and dried-out hair tends to be less shiny and more brittle. A protective moisture barrier on the hair will help to keep moisture in the hair allowing hair to keep its shine. Conversely, under high humidity conditions hair tends to absorb water causing hair to lose its shape and become unmanageable and unattractive. A protective moisture barrier on the hair will help keep moisture out of the hair under high humidity conditions leading to improved manageability. Such a protective barrier can also inhibit color fading in both dyed and naturally colored hair. This protective barrier can be applied to other keratinous substrates such as skin, lips, nails and eyelashes. The protective barrier is also useful in cosmetic applications such as makeup, skin care and sun care products. Such a protective barrier should be water-resistant so that the barrier is not easily removed. In addition, the protective barrier should not be easily transferred from the substrate over time by normal everyday activity. Accordingly, a product that provides a protective barrier to the substrate that also is water resistant and non-transferable would be of benefit to the area of cosmetic products.

BRIEF SUMMARY OF THE DISCLOSURE

The disclosure relates to compositions for treating keratinous substrates and methods of using the compositions to treat hair, skin, eyelashes, nails and lips. The disclosed compositions, which are opaque in nature, provide a water resistant and non-transferable protective barrier on the keratinous substrates imparting desirable properties to the substrate. The methods involve applying the compositions to the substrates. The compositions contain at least one polyamine, at least one acid, at least one water-insoluble ingredient, solvent and optionally at least one auxiliary ingredient. The methods for imparting desirable properties to the keratinous involve contacting the substrate with the compositions of the disclosure. Methods for improving the properties of keratinous substrates are also disclosed. Specifically, methods for improving the shine, condition and manageability of hair are disclosed. In addition, methods of inhibiting color fading in both dyed and naturally colored hair are also disclosed. Finally, methods of making-up eyelashes, making-up lips, making-up facial skin, making-up nails, making-up eyes, protecting skin from UV light damage and chemical damage, reducing the appearance of wrinkles and prolonging the efficacy of an active ingredient on a keratinous substrate are disclosed.

DETAILED DESCRIPTION OF THE DISCLOSURE

The term "comprising" (and its grammatical variations) as used herein is used in the inclusive sense of "having" or "including" and not in the exclusive sense of "consisting only of". The terms "a" and "the" as used herein are understood to encompass the plural as well as the singular.

Other than in the operating examples, or where otherwise indicated, all numbers expressing quantities of ingredients and/or reaction conditions are to be understood as being modified in all instances by the term "about".

The term "water-insoluble" means those compounds which are either completely or partially insoluble in water.

"At least one" as used herein means one or more and thus includes individual components as well as mixtures/combinations.

"Conditioning" as used herein means imparting to at least one keratinous fiber at least one property chosen from combability, manageability, moisture-retentivity, luster, shine, and softness. The state of conditioning is evaluated by measuring, and comparing, the ease of combability of the treated hair and of the untreated hair in terms of combing work (gm-in).

"Substituted," as used herein, means comprising at least one substituent. Non-limiting examples of substituents include atoms, such as oxygen atoms and nitrogen atoms, as well as functional groups, such as hydroxyl groups, ether groups, alkoxy groups, acyloxyalky groups, oxyalkylene groups, polyoxyalkylene groups, carboxylic acid groups, amine groups, acylamino groups, amide groups, halogen containing groups, ester groups, thiol groups, sulphonate groups, thiosulphate groups, siloxane groups, and polysiloxane groups. The substituent(s) may be further substituted.

The at least one polyamine of the disclosure comprises at least two amino groups and typically comprises at least five amino groups and more typically comprises at least ten amino groups.

The at least one acid comprises at least one acid group. The at least one acid may also comprise 2 or more acid groups (a polyacid).

Amino groups include primary amino groups, secondary amino groups and tertiary amino groups and further includes amino groups which are terminal, pendant and intercalated in a skeleton of the at least one polyamine compound.

In an embodiment of the disclosure the composition for treating a keratinous substrate comprises:
(a) at least one polyamine,
(b) at least one acid,
(b) at least one water-insoluble ingredient and
(d) solvent,
wherein the ratio of the amine number of the at least one polyamine to the acid number of the at least one acid is from about 1:0.5 to about 1:30 and wherein a mixture of components (a), (b), (c), and (d) form a mixture that has a contact angle of at least about 66 degrees on glass. Typically, the ratio of the amine number to the acid number is from about 1:0.8 to about 1:20 and more typically from about 1:0.9 to about 1:15 and even more typically from about 1:1 to about 1:10.

Another embodiment of the disclosure involves treating keratinous substrates with the disclosed composition. Such treatments impart desirable properties to the keratinous substrate.

Another embodiment of the disclosure involves treating hair with the disclosed composition to improve the shine, condition and manageability of the hair.

Another embodiment of the disclosure involves treating hair with the disclosed composition to inhibit color fading in dyed and naturally colored hair.

Another embodiment of the disclosure involves treating various keratinous substrates with the disclosed composition. The methods of treating keratinous substrates with the disclosed composition includes making-up eyelashes, making-up lips, making-up facial skin, making-up nails, making-up eyes, protecting skin from UV light damage and chemical damage, reducing the appearance of wrinkles and prolonging the efficacy of an active ingredient on a keratinous substrate.

The at least one polyamine (a) may, for example, be chosen from a polyethyleneimine, a polyvinylamine, an aminated polysaccharide, an amine substituted polyalkylene glycol, an amine substituted polyacrylate crosspolymer, an amine substituted polyacrylate, an amine substituted polymethacrylate, an aminosilicone, a protein, an amine substituted polyester, a polyamino acid, an amodimethicone, a polyalkylamine, diethylene triamine, triethylenetetramine, spermidine, spermine and mixtures thereof.

Non-limiting examples of polyethyleneimine include Lupasol® products commercially available from BASF. Suitable examples of Lupasol® polyethyleneimines include Lupasol® PS, Lupasol® PL, Lupasol® PR8515, Lupasol® G20, Lupasol® G35 as well as Lupasol® SC Polyethyleneimine Reaction Products (such as Lupasol® SC-61B, Lupasol® SC-62J, and Lupasol® SC-86X). Other non-limiting examples of polyethyleneimines which may be used in the composition according to the present invention are the Epomin® products commercially available from Aceto. Suitable examples of Epomin® polyethyleneimines include Epomin® SP-006, Epomin® SP-012, Epomin® SP-018, and Epomin® P-1000. These examples include substituted polyethyleneimines.

Non-limiting examples of polyvinylamines include Lupamines® 9095, 9030, 9010, 5095 and 1595 from BASF.

An example of an amine substituted polyalkylene glycol includes PEG-15 cocopolyamine from Cognis.

An example of an aminosilicone includes Dow Corning® 2-8566 Amino Fluid, an amino functional polydimethylsiloxane fluid from Dow Corning®.

In another embodiment, the at least one polyamine compound is chosen from proteins and protein derivatives. Non-limiting examples of suitable proteins and protein derivatives for use in the present invention include those listed at pages 1701 to 1703 of the C.T.F.A. International Cosmetic Ingredient Dictionary and Handbook, $8^{th}$ edition, vol. 2, (2000) (incorporated herein by reference). In one embodiment, the at least one polyamine compound is chosen from wheat protein, soy protein, oat protein, collagen, and keratin protein.

In another embodiment, the at least one polyamine compound is chosen from compounds comprising lysine, compounds comprising arginine, compounds comprising histidine, and compounds comprising hydroxylysine. Not limiting examples include chitosan, polyarginine and polylysine.

An example of an amine substituted polyacrylate crosspolymer includes Carbopol® Aqua CC polymer from Lubrizol Advanced Materials, Inc.

In the present disclosure, the at least one polyamine is used in a positive amount up to about 30% by weight, more typically a positive amount up to about 10% by weight, and most typically a positive amount up to about 5% by weight, based on the weight of the composition as a whole. In some embodiments the at least one polyamine ranges from about 0.1% to about 30% by weight based on the weight of the composition. In other embodiments the at least one polyamine ranges from about 0.1 wt % to about 10 wt %, based on the weight of the composition as a whole and in further embodiments the range is from about 0.1 wt % to about 5 wt %.

The at least one acid (b) of the composition may, for example, be chosen from a fatty carboxylic acid, a fatty ether carboxylic acid, a fatty ether phosphoric acid, a fatty phosphoric acid and mixtures thereof. The at least one acid (b) may contain one or 2 or more acid groups (a polyacid).

Non-limiting examples of fatty carboxylic acids includes fatty acids having from about 6 to about 40 carbon atoms corresponding formula (I)

RCOOH                                      (I)

wherein:

R is a hydrocarbon radical containing from about 6 to about 40 carbon atoms. In addition, R is linear or branched, acyclic or cyclic, saturated or unsaturated, aliphatic or aromatic, substituted or unsubstituted. Typically, R is a linear or branched, acyclic $C_{6-40}$ alkyl or alkenyl group or a $C_{1-40}$ alkyl phenyl group, more typically a $C_{8-22}$ alkyl or alkenyl group or a $C_{4-18}$ alkyl phenyl group, and even more typically a $C_{12-18}$ alkyl group or alkenyl group or a $C_{6-16}$ alkyl phenyl group.

Suitable fatty acids having from about 6 to about 40 carbon atoms include, but are not limited to the following representatives referred to by their INCI names (INCI: nomenclature for raw materials according to the International Cosmetic Ingredient Dictionary, $10^{th}$ Edition, published by the Cosmetic, Toiletry and Fragrance Association Inc. (CTFA), Washington D.C., USA): Arachidic Acid, Arachidonic Acid, Beeswax Acid, Capric Acid, Caproic Acid, Caprylic Acid, Coconut Acid, Isostearic Acid, Lauric Acid, Linoleic Acid, Linolenic Acid, Myristic Acid, Oleic Acid, Olive Acid, Palmitic Acid, Rapeseed Acid, Stearic Acid, Behenic Aid, Tallow Acid, Undecanoic Acid, Undecylenic Acid, 18-Methyleicosanoic Acid, Wheat Germ Acid and mixtures thereof.

Typical fatty acids having from about 6 to about 40 carbon atoms include Linoleic Acid, Oleic Acid, Isostearic Acid, and Stearic Acid.

Non-limiting examples of fatty ether carboxylic acid includes compounds corresponding to formula (II):

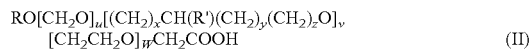

$RO[CH_2O]_u[(CH_2)_xCH(R')(CH_2)_y(CH_2)_zO]_v$
$[CH_2CH_2O]_wCH_2COOH$                      (II)

wherein:
R is a hydrocarbon radical containing from about 6 to about 40 carbon atoms;
u, v and w, independently of one another, represent numbers of from 0 to 60;
x, y and z, independently of one another, represent numbers of from 0 to 13;
R' represents hydrogen, alkyl, and
the sum of x+y+z is ≥0;

Ether carboxylic acids corresponding to formula (II) can be obtained by alkoxylation of alcohols ROH with ethylene oxide as the sole alkoxide or with several alkoxides and subsequent oxidation. The numbers u, v, and w each represent the degree of alkoxylation. Whereas, on a molecular level, the numbers u, v and w and the total degree of alkoxylation can only be integers, including zero, on a macroscopic level they are mean values in the form of broken numbers.

In formula (II), R is linear or branched, acyclic or cyclic, saturated or unsaturated, aliphatic or aromatic, substituted or unsubstituted. Typically, R is a linear or branched, acyclic $C_{6-40}$ alkyl or alkenyl group or a $C_{1-40}$ alkyl phenyl group, more typically a $C_{8-22}$ alkyl or alkenyl group or a $C_{4-18}$ alkyl phenyl group, and even more typically a $C_{12-18}$ alkyl group or alkenyl group or a $C_{6-16}$ alkyl phenyl group; u, v, w, independently of one another, is typically a number from 2 to 20, more typically a number from 3 to 17 and most typically a number from 5 to 15; x, y, z, independently of one another, is typically a number from 2 to 13, more typically a number from 1 to 10 and most typically a number from 0 to 8.

Suitable ether carboxylic acids or ether carboxylates include, but are not limited to, the following representatives referred to by their INCI names (INCI: nomenclature for raw materials according to the International Cosmetic Ingredient Dictionary, $7^{th}$ Edition, published by the Cosmetic, Toiletry and Fragrance Association Inc. (CTFA), Washington D.C., USA): Butoxynol-5 Carboxylic Acid, Butoxynol-19 Carboxylic Acid, Capryleth-4 Carboxylic Acid, Capryleth-6 Carboxylic Acid, Capryleth-9 Carboxylic Acid, Ceteareth-25 Carboxylic Acid, Coceth-7 Carboxylic Acid, $C_{9-11}$ Pareth-6 Carboxylic Acid, $C_{11-15}$ Pareth-7 Carboxylic Acid, $C_{12-13}$ Pareth-5 Carboxylic Acid, $C_{12-13}$ Pareth-8 Carboxylic Acid, $C_{12-13}$ Pareth-12 Carboxylic Acid, $C_{12-15}$ Pareth-7 Carboxylic Acid, $C_{12-15}$ Pareth-8 Carboxylic Acid, $C_{14-15}$ Pareth-8 Carboxylic Acid, Deceth-7 Carboxylic Acid, Laureth-3 Carboxylic Acid, Laureth-4 Carboxylic Acid, Laureth-5 Carboxylic Acid, Laureth-6 Carboxylic Acid, Laureth-8 Carboxylic Acid, Laureth-10 Carboxylic Acid, Laureth-11 Carboxylic Acid, Laureth-12 Carboxylic Acid, Laureth-13 Carboxylic Acid, Laureth-14 Carboxylic Acid, Laureth-17 Carboxylic Acid, PPG-6-Laureth-6 Carboxylic Acid, PPG-8-Steareth-7 Carboxylic Acid, Myreth-3 Carboxylic Acid, Myreth-5 Carboxylic Acid, Nonoxynol-5 Carboxylic Acid, Nonoxynol-8 Carboxylic Acid, Nonoxynol-10 Carboxylic Acid, Octeth-3 Carboxylic Acid, Octoxynol-20 Carboxylic Acid, Oleth-3 Carboxylic Acid, Oleth-6 Carboxylic Acid, Oleth-10 Carboxylic Acid, PPG-3-Deceth-2 Carboxylic Acid, Capryleth-2 Carboxylic Acid, Ceteth-13 Carboxylic Acid, Deceth-2 Carboxylic Acid, Hexeth-4 Carboxylic Acid, Isosteareth-6 Carboxylic Acid, Isosteareth-11 Carboxylic Acid, Trudeceth-3 Carboxylic Acid, Trideceth-6 Carboxylic Acid, Trideceth-8 Carboxylic Acid, Trideceth-12 Carboxylic Acid, Trideceth-3 Carboxylic Acid, Trideceth-4 Carboxylic Acid, Trideceth-7 Carboxylic Acid, Trideceth-15 Carboxylic Acid, Trideceth-19 Carboxylic Acid, Undeceth-5 Carboxylic Acid and mixtures thereof.

Typical Carboxylic Acids are Oleth-10 Carboxylic Acid, Laureth-5 Carboxylic Acid and Laureth-11 Carboxylic Acid.

Non-limiting examples of fatty phosphoric acids include compounds corresponding to Formula III:

$$R\text{—}O\text{—}P(O)(OH)_2 \quad \text{(III)}$$

wherein:

R is a hydrocarbon radical containing from about 6 to about 40 carbon atoms. In addition, R is linear or branched, acyclic or cyclic, saturated or unsaturated, aliphatic or aromatic, substituted or unsubstituted. Typically, R is a linear or branched acyclic $C_{6-40}$ alkyl or alkenyl group or a $C_{1-40}$ alkyl phenyl group, more typically a $C_{8-22}$ alkyl or alkenyl group or a $C_{4-18}$ alkyl phenyl group and most typically a $C_{12-18}$ alkyl group or alkenyl group or a $C_{6-16}$ alkyl phenyl group.

Typical fatty phosphoric acids include capryl phosphate, caprylyl phosphate, lauryl phosphate, oleyl phosphate, isostearyl phosphate, stearyl phosphate and cetyl phosphate.

Non-limiting examples of fatty ether phosphoric acids compounds corresponding to formulas IV and V:

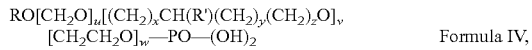

$$RO[CH_2O]_u[(CH_2)_xCH(R')(CH_2)_y(CH_2)_zO]_v \\ [CH_2CH_2O]_w\text{—}PO\text{—}(OH)_2 \quad \text{Formula IV,}$$

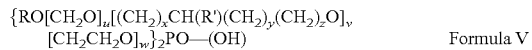

$$\{RO[CH_2O]_u[(CH_2)_xCH(R')(CH_2)_y(CH_2)_zO]_v \\ [CH_2CH_2O]_w\}_2PO\text{—}(OH) \quad \text{Formula V}$$

and combinations thereof,
wherein:
R is a hydrocarbon radical containing from about 6 to about 40 carbon atoms;
u, v and w, independently of one another, represent numbers of from 0 to 60;
x, y and z, independently of one another, represent numbers of from 0 to 13;
R' represents hydrogen, alkyl, and
the sum of x+y+z being ≥0.

The numbers u, v, and w each represent the degree of alkoxylation. Whereas, on a molecular level, the numbers u, v and w and the total degree of alkoxylation can only be integers, including zero, on a macroscopic level they are mean values in the form of broken numbers.

In formulas IV and V, R is linear of branched, acyclic or cyclic, saturated or unsaturated, aliphatic or aromatic, substituted or unsubstituted, typically a linear or branched, acyclic $C_{6-40}$ alkyl or alkenyl group or a $C_{1-40}$ alkyl phenyl group, more typically a $C_{8-22}$ alkyl or alkenyl group or a $C_{4-18}$ alkyl phenyl group, even more typically a $C_{12-18}$ alkyl group or alkenyl group or a $C_{6-16}$ alkyl phenyl group; u, v, w, independently of one another, is typically a number from 2 to 20, more typically a number from 3 to 17 and most typically a number from 5 to 15; x, y, z, independently of one another, is typically a number from 2 to 13, more typically a number from 1 to 10 and most typically a number from 0 to 8.

Typical fatty ether phosphoric acids include PPG-5-Ceteth-10 phosphate (CRODAFOS SG), Oleth-3 phosphate (CRODAFOS N3 acid), Oleth-10 phosphate (CRODAFOS N10 acid), and a mixture of Ceteth-10 phosphate and Dicetyl phosphate (CRODAFOS CES) all sold by Croda.

Examples of the at least one acid (b) that contain 2 or more acid groups include Acrylates Copolymer, Acrylates/Octylacrylamide Copolymer, Acrylates/Octylacrylamide/Diphenyl Amodimethicone Copolymer, Octylacrylamide/acrylates/Butylaminoethyl Methacrylate Copolymer, Acrylates/Stearyl Acrylate/Ethylamine Oxide Methacrylate Copolymer, Acrylates/t-Butylacrylamide Copolymer, PEG/PPG-25/25 Dimethicone/Acrylates Copolymer, VA/Butyl Maleate/Isobornyl Acrylate Copolymer, PVM/MA Copolymer, Ethyl ester of PVM/MA Copolymer, Butyl Ester of PVM/MA Copolymer, VA/Crotonates Copolymer, VA/Crotonates/Vinyl Neodecanoate Copolymer, VA/Vinyl Butyl Benzoate/Crotonates Copolymer, Carbomer, Polystyrene sulfonic acid, Terephthalylidene Dicamphor Sulfonic Acid, Phenylbenzimidazole Sulfonic Acid, Polyacrylamidomethylpropane Sulfonic Acid, Dimethicone PEG-7 Phosphate, Dimethicone PEG-8 Phosphate, Dimethicone PEG-10 Phosphate, Dimethicone PEG/PPG-7/4 Phosphate, Dimethicone PEG/PPG-12/4 Phosphate, Lauryl dimethicone PEG-10 Phosphate, Polyperfluoroethoxymethoxy Difluoroethyl PEG Phosphate, Polyperfluoroethoxymethoxy PEG-2 Phosphate, Polyphosphorylcholine Glycol Acrylate, Cocoamphodipropionic Acid, Lauroamphodipropionic Acid, Lauriminodipropionic Acid, Polyacrylic Acid, Polymethacrylic Acid, Polyglutamic acid, Myristoyl Glutamic Acid, Lauroyl Glutamic Acid, Palmitoyl Glutamic Acid, Cocoyl Glutamic Acid.

The at least one acid (b) is present in the composition in a positive amount up to about 50% by weight, typically a positive amount up to about 30% by weight, and more typically a positive amount up to about 15% by weight, based on the weight of the composition as a whole. In other embodiments, the at least one acid (b) is present in the composition in a range of from about 2% to about 50% by weight and in a range from about 5% to about 15% by weight, based on the weight of the composition as a whole.

The at least one water-insoluble ingredient (c) may, for example, be chosen from an oil, a polymer, a fatty ester, a hydrocarbon, a silicone, a wax, a fatty acid (in addition to the fatty acid (a)), salts of fatty acids, a fatty alcohol and mixtures thereof.

Non-limiting examples of oils include plant oil such as olive oil, avocado oil, coconut oil, aloe vera oil, almond oil, castor oil, jojoba oil, peanut oil, sesame oil, hazelnut oil, sunflower oil, colza oil, grapeseed oil, linseed oil and palm oil.

Non-limiting examples of hydrocarbon oils include mineral oil, petrolatum, paraffins, iso-paraffins, aromatic hydrocarbons and $C_{10-40}$ hydrocarbons which may be aliphatic, aromatic, arylaliphatic or mixtures thereof and the aliphatic hydrocarbons may be straight chain, branched, cyclic or combinations thereof.

Non-limiting examples of silicones include phenyltrimethicone, dimethicone, cyclomethicone, dimethicone copolyol, aminosilicone, laurylmethicone copolyol, cetyl dimethicone, cetyl triethylammonium dimethicone copolyol phthalate, dimethicone copolyol lactate, silicone quaternium-13, stearalkonium dimethicone copolyol phthalate, stearaminopropyl dimethicone and polyorganosiloxanes such as polydimethylsiloxane.

Non-limiting examples of waxes include paraffin wax, beeswax, candelilla wax, carnauba wax, jasmine wax, jojoba wax and mimosa wax.

Non-limiting examples of fatty acids are the same as those described above for the at least one fatty acid described above. This includes carboxylate salts of the fatty acids listed above. The sodium, potassium, ammonium, calcium and magnesium carboxylates of the fatty acids listed above are typical examples of the carboxylate salts of the fatty acids.

Non-limiting example of fatty alcohols include compounds of formula (VI):

$$R—OH \quad (VI)$$

where R is as described above for the at least one fatty acid.

Non-limiting fatty esters include esters formed from the fatty acid of formula (I) and $C_{1-22}$ alcohols and esters formed from the fatty alcohol of formula VI and $C_{1-22}$ carboxylic acids.

In addition, non-limiting specific examples of water-insoluble ingredients includes isopropyl palmitate, capric/caprylic triglyceride, isododecane, polyIsobutylene, tocopherol, tocopherol acetate, retinol, retinyl palmitate, 2-oleamido-1,3-octadecanediol, octymethoxy cinnamate, octyl salicylate, 18-Methyleicosanoic Acid and mixtures thereof.

The at least one water-insoluble ingredient (c) is present in the composition in a positive amount up to about 50% by weight, typically a positive amount up to about 30% by weight, and more typically a positive amount up to about 15% by weight based on the weight of the composition as a whole. In other embodiments, the at least one water-insoluble ingredient (c) is present in the composition in an amount from about 0.1 to about 50% by weight and in an amount from about 0.5 to about 15% by weight based on the weight of the composition as a whole.

Solvent (d) in the composition is present in an amount from about 10% by weight to about 95% by weight, typically in an amount from about 50% by weight to about 85% by weight and more typically from about 60% by weight to 80% by weight, based on the weight of the composition as a whole. The solvent is typically water, alcohol, glycol or mixtures thereof. Alcohols include ethanol, propanol and butanol. Typically, the alcohol is ethanol or isopropanol. Glycols include hexylene glycol, diethylene glycol, ethylene glycol, propylene glycol, 1,2-butylene glycol, triethylene glycol, dipropylene glycol, and mixtures thereof.

The composition may optionally contain at least one auxiliary ingredient (e) in a positive amount up to about 50% by weight, based on the weight of the composition. The auxiliary ingredient may include proteins, amino acids cationic conditioners, cationic polymers, nonionic surfactants, anionic surfactants, amphoteric surfactants, zwitterionic surfactants, viscosity modifiers, organosiloxane polymer, waxes, silicone resins, pigments, powders, preservatives, vitamins, antioxidants, alpha hydroxyl acids, beta hydroxyl acids, alpha keto acids, antibacterial agents, sunscreens, preservatives, pH adjusting agents, bleaching agents, perfumes, sequestering agents, anti-dandruff agents and mixtures thereof.

Non-limiting examples of proteins include collagen, deoxyribonuclease, iodized corn protein, milk protein, protease, serum protein, silk, sweet almond protein, wheat germ protein, wheat protein, alpha and beta helix of keratin proteins, hair proteins, such as intermediate filament proteins, high-sulfur proteins, ultrahigh-sulfur proteins, intermediate filament- associated proteins, high-tyrosine proteins, high-glycine tyrosine proteins, tricohyalin, and mixtures thereof.

Non-limiting examples of amino acids include amino acids derived from the hydrolysis of various proteins as well as the salts, esters, and acyl derivatives thereof. Non-limiting examples of such amino acid agents include amphoteric amino acids such as alkylamido alkylamines, i.e. stearyl acetyl glutamate, capryloyl silk amino acid, capryloyl collagen amino acids, capryloyl keratin amino acids, capryloyl pea amino acids, cocodimonium hydroxypropyl silk amino acids, corn gluten amino acids, cysteine, glutamic acid, glycine, hair keratin amino acids, amino acids such as asparatic acid, threonine, serine, glutamic acid, proline, glycine, alanine, cystine, valine, methionine, isoleucine, leucine, tyrosine, phenylalanine, cysteic acid, lysine, histidine, arginine, cysteine, tryptophan, citrulline, lysine, silk amino acids, wheat amino acids and mixtures thereof.

Non-limiting examples of cationic conditioners include quaternium-27, behenamidopropyl PG-dimonium chloride, hydroxyethyl tallowdimonium chloride, hexadimethrine chloride, stearalkonium chloride and cetrimonium chloride.

Conditioning agents may also be chosen from amino acids, proteins, extracts, fats, oils, esters, transesters, hydrocarbons, quats, polyquats, zwitterionic surfactants, amphoteric surfactants, alcohols, polyols, humectants, alkanolamides, fatty acids, ketones, and mixtures thereof. The conditioning agent is present in an amount from about 0.001% to about 50% by weight, based on the weight of the composition. Typically, the conditioning agent is present in an amount from about 0.1% to about 35% by weight, based on the weight of the composition and more typically in an amount from about 1% to about 20% by weight, based on the weight of the composition.

Non-limiting examples of conditioning agents include Arginine, Asparagine, Aspartic Acid, Carnitine, Cocoyl sarcosine, Glycine, Glutamic acid, Histidine, Hydroxyproline, Acetyl Hydroxy praline, Isoleucine, Lysine, Lauroyl Lysine, Lauroyl Sarcosine, Methionine, Phenylalanine, Polylysine, Potassium Cocoyl Glutamate, Proline, Sarcosine, Serine , Rice amino acids, Silk amino acids, Wheat amino aids, Sodium Glutamate, Sodium Lauroyl Glutamate, Sodium PCA, Stearoyl sarcosine, Threonine, Tyrosine, Tryptophan, Valine, Casein, Collagen, Procollagen, Gelatin, Keratin, Glycoproteins, Hydrolyzed wheat protein, Hydrolyzed soy protein, Hydrolyzed oat protein, Hydrolyzed rice protein, Hydrolzed vegetable protein, Hydrolyzed yeast protein, Whey protein, Ginkgo Biloba Nut extract, Salix Alba (Willow) Bark Extract, Morus Alba (Mulberry) Leaf, Behentrimonium Chloride, Behenamidopropyl PG-Dimonium Chloride, Behentrimonium Methosulfate, Cocotrimonium Methosulfate, Olealkonium Chloride, Steartrimonium Chloride, Babassuamidopropalkonium Chloride, Hydroxypropyl Guar, Hydroxypropyltrimonium chloride, Laurdimonium Hydroxypropyl Hydrolyzed Soy Protein, Steardimonium Hydroxypropyl Hydrolyzed Wheat Protein, Quaternium-22, Quaternium-27, Quaternium-87, Polyquaternium-4, Polyquaternium-6, Polyquaternium-10, Polyquaternium-11, Polyquaternium-44, Polyquaternium-67, Silicone Quaterium-8, Amodimethicone, Aminopropyldimethicone, Phenyltrimethicone, Cyclomethicone, Dimethicone, Hexyl Dimethicone, Dilinoleamidopropyl Dimthylamine Dimethicone PEG-7 Phosphate, C26-28 Alkyl Dimethicone, PEG-8 Dimethicone, PPG-12 Dimethicone, Polysilicone-13, Trideceth-9 PG-Amodimethicone, Bis-PEG-12 Dimethicone Beeswax, Capric/Caprylic Triglyceride, Petrolatum, Mineral Oil, Lanolin Oil, Cocos nucifera (Coconut) Oil, Olea Europea (Olive) Fruit Oil , Simmondsia Chinensis (Jojoba) Seed Oil, Prunus Armeniaca (Apricot) Kernel Oil, Crambe Abyssinica Seed Oil, Vegetable Oil, Zea Mays (Corn) Oil, Acetylated Lanolin Alcohol, Cetearyl Isononanoate, Cetearyl Ethylhexanoate, Cetearyl Palmitate, Hydrogenated Olive Oil Hexyl Esters, Triethylhexanoin, Ceramide-3, Caprylyl Glycol, Cetyl Glycol, Glycerin, Panthenol, Phytantriol, Methanediol, Inositol, PPG-35-Buteth-45, PPG-5 Butyl Ether, Cocoamidopropyl Betaine, Coco-Betaine, Cocoamidopropyl Hydroxysultaine, Lauramidopropyl Betaine, Lauryl Betaine, Oleamidopropyl Betaine, Disodium Cocoamphodiacetate, Disodium Cocoamphodipropionate, Disodium Lauroamphodiacetate, Sodium Cocoamphopropionate, Sodium Cocoamphoacetate, Acetamide MEA, Behenamide MEA, Linoleamide DEA, Linoleamide MEA, Linoleamide MIPA, Linoleic Acid, Linolenic Acid, Maltodextrin, Niacin, Polyacrylate-1 Crosspolymer, Polyester-4, Pyridoxine HCl, Phytosphingosine, Salicylic Acid, Squalane, Squalene, Thiodiglycoamide, Zinc Pyrithione, and mixtures thereof.

Non-limiting examples of cationic polymers include polyquaternium-4, polyquaternium-6, polyquaternium-7, polyquaternium-10, polyquaternium-11, polyquaternium-16, polyquaternium-22 and polyquaternium-32.

Non-limiting examples of nonionic surfactants includes alkoxylated derivatives of the following: fatty alcohols, alkyl phenols, fatty acids, fatty acid esters and fatty acid amides, wherein the alkyl chain is in the $C_{12-50}$ range, typically in the $C_{16-40}$ range, more typically in the $C_{24}$ to $C_{40}$ range, and having from about 1 to about 110 alkoxy groups. The alkoxy groups are selected from the group consisting of $C_2$-$C_6$ oxides and their mixtures, with ethylene oxide, propylene oxide, and their mixtures being the typical alkoxides. The alkyl chain may be linear, branched, saturated, or unsaturated. Of these alkoxylated non-ionic surfactants, the alkoxylated alcohols are typical, and the ethoxylated alcohols and propoxylated alcohols are more typical. The alkoxylated alcohols may be used alone or in mixtures with those alkoxylated materials disclosed herein-above.

Other representative examples of such ethoxylated fatty alcohols include laureth-3 (a lauryl ethoxylate having an average degree of ethoxylation of 3), laureth-23 (a lauryl ethoxylate having an average degree of ethoxylation of 23), ceteth-10 (a cetyl alcohol ethoxylate having an average degree of ethoxylation of 10), steareth-10 (a stearyl alcohol ethoxylate having an average degree of ethoxylation of 10), steareth-2 (a stearyl alcohol ethoxylate having an average degree of ethoxylation of 2), steareth-100 (a stearyl alcohol ethoxylate having an average degree of ethoxylation of 100), beheneth-5 (a behenyl alcohol ethoxylate having an average degree of ethoxylation of 5), beheneth-10 (a behenyl alcohol ethoxylate having an average degree of ethoxylation of 10), and other derivatives and mixtures of the preceding.

Commercially available nonionic surfactants are Brij® nonionic surfactants from Uniqema, Willmington, Del. Typically, Brij® is the condensation products of aliphatic alcohols with from about 1 to about 54 moles of ethylene oxide, the alkyl chain of the alcohol being typically a linear chain and having from about 8 to about 22 carbon atoms, for example, Brij 72 (i.e., Steareth-2) and Brij 76 (i.e., Steareth-10).

Also useful herein as nonionic surfactants are alkyl glycosides, which are the condensation products of long chain alcohols, which are the condensation products of long chain alcohols, e.g. $C_8$-$C_{30}$ alcohols, with sugar or starch polymers. These compounds can be represented by the formula (S)n-O—R wherein S is a sugar moiety such as glucose, fructose, mannose, galactose, and the like; n is an integer of from about 1 to about 1000, and R is a $C_8$-$C_{30}$ alkyl group. Examples of long chain alcohols from which the alkyl group can be derived include decyl alcohol, cetyl alcohol, stearyl alcohol, lauryl alcohol, myristyl alcohol, oleyl alcohol, and the like. Preferred examples of these surfactants are alkyl polyglucosides wherein S is a glucose moiety, R is a $C_8$-$C_{20}$ alkyl group, and n is an integer of from about 1 to about 9. Commercially available examples of these surfactants include decyl polyglucoside (available as APG® 325 CS) and lauryl polyglucoside (available as APG® 600CS and 625 CS), all the above-identified polyglucosides APG® are available from Cognis, Ambler, Pa. Also useful herein sucrose ester surfactants such as sucrose cocoate and sucrose laurate.

Other nonionic surfactants suitable for use in the present invention are glyceryl esters and polyglyceryl esters, including but not limited to, glyceryl monoesters, typically glyceryl monoesters of $C_{16}$-$C_{22}$ saturated, unsaturated and branched chain fatty acids such as glyceryl oleate, glyceryl monostearate, glyceryl monoisostearate, glyceryl monopalmitate, glyceryl monobehenate, and mixtures thereof, and polyglyceryl esters of $C_{16}$-$C_{22}$ saturated, unsaturated and branched chain fatty acids, such as polyglyceryl-4 isostearate, polyglyceryl-3 oleate, polyglyceryl-2 sesquioleate, triglyceryl diisostearate, diglyceryl monooleate, tetraglyceryl monooleate, and mixtures thereof.

Also useful herein as nonionic surfactants are sorbitan esters. Preferable are sorbitan esters of $C_{16}$-$C_{22}$ saturated, unsaturated and branched chain fatty acids. Because of the manner in which they are typically manufactured, these sorbitan esters usually comprise mixtures of mono-, di-, tri-, etc. esters. Representative examples of suitable sorbitan esters include sorbitan monooleate (e.g., SPAN® 80), sorbitan sesquioleate (e.g., Arlacel® 83 from Uniqema, Wilmington, Del.), sorbitan monoisostearate (e.g., CRILL® 6 from Croda, Inc., Edison, N.J.), sorbitan stearates (e.g., SPAN® 60), sorbitan trioleate (e.g., SPAN® 85), sorbitan tristearate (e.g., SPAN® 65), sorbitan dipalmitates (e.g., SPAN® 40), and sorbitan isostearate. Sorbitan monoisostearate and sorbitan sesquioleate are particularly preferred emulsifiers for use in the present invention.

Also suitable for use as nonionic surfactants are alkoxylated derivatives of glyceryl esters, sorbitan esters, and alkyl polyglycosides, wherein the alkoxy groups is selected from the group consisting of $C_2$-$C_6$ oxides and their mixtures, with ethoxylated or propoxylated derivatives of these materials being typical. Non-limiting examples of commercially available ethoxylated materials include TWEEN® (ethoxylated sorbitan mono-, di- and/or tri-esters of $C_{12}$ to $C_{18}$ fatty acids with an average degree of ethoxylation of from about 2 to 20).

Non-limiting examples of anionic surfactants include compounds in the classes known as alkyl sulfates, alkyl ether sulfates, alkyl sulfonates, alkyl ether sulfonates, sulfate esters of an alkylphenoxy polyoxyethylene ethanol, alpha-olefin sulfonates, beta alkyloxy alkene sulfonates, alkyl arylsulfonates, alkyl carbonates, alkyl ether carboxylates, fatty acids, succinamates, sulfosuccinates, sarcosinates, octoxynol or nonoxynol phosphates, taurates, fatty taurides, sulfated monoglycerides, fatty acid amino polyoxyethylene sulfates, isothienates and mixtures thereof. Specific examples of anionic surfactants include the ammonium, monoethanolamine, diethanolamine, triethanolamine, isopropylamine, sodium, potassium, lithium, or magnesium salts of lauryl sulfate, dodecylbenzene-sulfonate, lauryl sulfosuccinate, lauryl ether sulfate, lauryl ether carboxylate, lauryl sarcosinate, cocomethyl tauride, and sulfosuccinate half ester amide and mixtures thereof.

Non-limiting examples of amphoteric and zwitterionic surfactants include alkyl, alkyl dimethyl, alkylamido, alkyl amide, alkylamidopropyl, or alkyl dimethylammonium betaine; alkyl amidopropyl or alkyl sulfobetaine; alkyl, alkylampho, or alkylamphocarboxy glycinate; alkyl, or alkyl substituted imidazoline mono or dicarboxylate; sodium salts of alkyl mono-or dicarboxylates; alkyl beta amino acids; alkyl amidopropyl, or alkyl ether hydroxysultaine; alkyl amidopropyl dimethyl ammonia acetate; alkyl ampho mono-or diacetate; alkyl, or alkyl ampho, or alkyl imino dipropionate; alkyl amphopropionate; alkyl beta amino propionic acid; alkyl dipropionate; alkyl beta iminodipropionate; branched or n-alkyl dimethylamidopropionate; alkyl carboxylated propionate; alkyl, or methyl alkyl imidazoline; fluorinated alkyl amphoteric mixtures; and/or nonionic surfactants such as, but not limited to, alkyl, alkyl dimethyl, alkyl amidopropylamine, or bis 2-hydroxy ethyl alkyl amine oxides; alkanolamides; alkyl amides; polyoxyethylene glycol (PEG) of monoglycerides, of sorbitan esters, of branched or linear fatty alcohol ethers, of branched or linear fatty acid ethers, of thioethers; alkyl oxoalcohol PEG; PEG fatty esters; polyoxyethlyene glycol/polyoxpropylene glycol block copolymers; alkyl phenol PEG ethers; alkyl polyglucosides, or polysaccharides, polysiloxane polyethoxylene ether and mixtures thereof.

Specific examples include cocamidopropyl betaine, lauramidopropyl betaine, coco/oleamidopropyl betaine, lauryl betaine, coco betaine, oleyl betaine, cocamidopropyl hydroxysultaine, tallowamidopropyl hydroxysultaine, dihydroxyethyl tallow glycinate, disodium cocoamphodiacetate, disodium cocoamphodipropionate and mixtures thereof.

Non-limiting examples of viscosity modifiers include water swellable/soluble cationic polymers from quaternized polysaccharides such as trimethyl ammonium substituted epoxide of hydroxyethyl cellulose, diallyl dimethyl ammonium salts of hydroxyethylcellulose, deacylated chitin or chitosan, dihydroxypropyl chitosan trimonium chloride, hydroxyprolytrimethyl ammonium chloride guar, locust bean, or konjac mannan gum; quaternized synthetics such as acrylamide dimethyl diallyl ammonium chloride copolymers, acrylamide/dimethyl diallyl ammonium chloride/acrylic acid terpolymer, quaternized poly(vinyl pyrrolidone/dimethyl amino ethylmethacrylate), poly(vinylpyrrolidone/methacrylamidopropyl trimethylammonium chloride), polyvinyl pyrrolidone/methylvinylimidazolinium chloride or methyl sulfate copolymer, chloroethylether/dimethylaminopropylamine/adipate or azelate terpolymer, vinylpyrrolidone/methacrylamidopropyl trimethylammonium chloride, acrylonitrile/acrylic acid/dimethylpropanediammonium acrylates sulfate terpolymer. Anionic or nonionic polysaccharide polymers such as gum tragacanth, sodium or propylene glycol alginate, kappa-, iota-, or lambda-carrageenan, guar or hydroxyl propyl guar gum, karaya gum, gum Arabic, locust bean gum, konjac mannan gum, gellan, xanthan, succinoglycan or its acidic or enzymatic hydrolysates, sodium carboxymethyl cellulose, methycellulose, hydroxylethylcellulose, hydroxypropylmethylcellulose, and hydroxypropylecellulose; and/or hydrophobically modified anionic, cationic, or nonionic polymers such as, but not limited to, alkyl and/or substituted hydroxyethylcellulose, lauryl dimethyl ammonium substituted epoxide of hydroxyethylcellulose, propoxylated cellulosic, xanthan, succinoglycan, or polygalactomannoses, alkyl methacrylates/crosslinked acrylic acid copolymer and/or acrylonitrile/acrylates block copolymer.

Examples of organosiloxane polymers useful in the disclosure are commercially available from Goldschmidt Corporation under the ABIL tradename. One typical example is cetyl dimethicone copolyol and has the tradename ABIL WE 09 or ABIL WS 08. The cetyl dimethicone copolyol may be used alone or in conjunction with other non-silicone organic emulsifiers. For example, the cetyl dimethicone copolyol may be used in an admixture with other non-silicone organic auxiliary ingredients such a emulsifiers and emollients. For example, the mixtures identified by the C.T.F.A. names cetyl dimethicone copolyol (and) polyglyceryl 4-isostearate (and) hexyl laurate, or cetyl dimethicone copolyol (and) polyglyceryl-3 oleate (and) hexyl laurate both work well. These blends contain approximately 25-50% of each ingredient, for example ABIL WE 09 contains approximately, by weight of the total ABIL composition, 25-50% cetyl dimethicone copolyol, 25-50%, polyglyceryl 4-isostearate, and 25-50% of hexyl laurate which is an emollient or oil.

Another type of organosiloxane polymer suitable for use in the compositions of the disclosure is sold by Union Carbide under the Silwet™ trademark. These compositions are represented by the following generic formulas:

(Me$_3$Si)$_y$-2[(OSiMe$_2$)$_x$/$_y$O-PE]$_y$ wherein PE=-(EO)$_m$(PO)$_n$R
R=lower alkyl or hydrogen
Me=methyl
EO is polyethyleneoxy
PO is polypropyleneoxy m and n are each independently 1-5000
x and y are each independently 0-5000, and 8
wherein PE=—CH$_2$CH$_2$CH$_2$O(EO)$_m$(PO)$_n$Z
Z=lower alkyl or hydrogen, and
Me, m, n, x, y, EO and PO are as described above,
with the proviso that the molecule contains a lipophilic portion and a hydrophilic portion. Again, the lipophilic portion can be supplied by a sufficient number of methyl groups on the polymer backbone.

Examples of other polymeric organosiloxane surfactants or emulsifiers include amino/polyoxyalkyleneated polydiorganosiloxanes disclosed in U.S. Pat. No. 5,147,578. Also suitable are organosiloxanes sold by Goldschmidt under the ABIL trademark including ABIL B-9806, as well as those sold by Rhone-Poulenc under the Alkasil tradename. Also, organosiloxane polymers sold by Amerchol under the Amersil tradename, including Amersil ME-358, Amersil DMC-287 and Amersil DMC-357 are suitable. Dow Corning surfactants such as Dow Corning 3225C Formulation Aid, Dow Corning 190 Surfactant, Dow Corning 193 Surfactant, Dow Corning Q2-5200, and the like are also suitable. In addition, products sold under the tradename Silwet by Union Carbide, and products sold by Troy Corporation under the Troysol tradename, those sold by Taiwan Surfactant Co. under the tradename Ablusoft, those sold by Hoechst under the tradename Arkophob, are also suitable for use in the disclosure.

The compositions of the disclosure may contain wax at a concentration about 0.1-25%, preferably 0.5-20%, more typically 1-15% by weight based on the total weight of the composition. Suitable waxes have a melting point of 35 to 120° C., and can be animal waxes, plant waxes, mineral waxes, silicone waxes, synthetic waxes, and petroleum waxes. Examples of waxes in accordance with the disclosure include bayberry, beeswax, candelilla, carnauba, ceresin, cetyl esters, hydrogenated jojoba oil, hydrogenated jojoba wax, hydrogenated microcrystalline wax, hydrogenated rice bran wax, japan wax, jojoba butter, jojoba esters, jojoba wax, lanolin wax, microcrystalline wax, mink wax, montan acid wax, montan wax, ouricury wax, ozokerite, paraffin, PEG-6 beeswax, PEG-8 beeswax, rice bran wax, shellac wax, spent grain wax, sulfurized jojoba oil, synthetic beeswax, synthetic candelilla wax, synthetic carnauba wax, synthetic japan wax, synthetic jojoba oil, ethylene homo- or copolymers, stearoxy dimethicone, dimethicone behenate, stearyl dimethicone, and the like, as well synthetic homo- and copolymer waxes such as PVP/eicosene copolymer, PVP/hexadecene copolymer, and the like.

Silicone resins in the compositions of the disclosure may be added at a concentration in a range of about 0.001-20%, typically 0.01-15%, more typically 0.1-10% by weight based on the total weight of the composition. Examples of suitable silicone resins include siloxy silicate polymers having the following general formula:

[(RR'R")$_3$SiO$_{1/2}$]$_x$[SiO$_2$]$_y$ wherein R, R' and R" are each independently a C$_{1-10}$ straight or branched chain alkyl or phenyl, and x and y are such that the ratio of (RR'R")$_3$SiO$_{1/2}$ units to SiO$_2$ units is 0.5 to 1 to 1.5 to 1.

Typically R, R' and R" are a C$_{1-6}$ alkyl, and more preferably are methyl and x and y are such that the ratio of (CH$_3$)$_3$SiO$_{1/2}$ units to SiO$_2$ units is 0.75 to 1. For example, a trimethylsiloxy silicate containing 2.4 to 2.9 weight percent hydroxyl groups which is formed by the reaction of the sodium salt of silicic acid, chlorotrimethylsilane, and isopropyl alcohol may be used. The manufacture of trimethylsiloxy silicate is set forth in U.S. Pat. Nos. 2,676,182; 3,541,205; and 3,836,437, all of which are hereby incorporated by reference. Trimethylsiloxy silicate as described is available from Dow Corning Corporation under the tradename 2-0749 and 2-0747, which is a blend of about 40-60% volatile silicone and 40-60% trimethylsiloxy silicate. Dow Corning 2-0749 in particular, is a fluid containing about 50% trimethylsiloxy silicate and about 50% cyclomethicone. The fluid has a viscosity of 200-700 centipoise at 25° C., a specific gravity of 1.00 to 1.10 at 25° C., and a refractive index of 1.40-1.41.

Other silicone resins are silicone esters comprising units of the general formula $R_a R^E_b SiO_{[4-(a+b)/2]}$ or $R^{13}_x R^E_y SiO_{1/2}$, wherein R and $R^{13}$ are each independently an organic radical such as alkyl, cycloalkyl, or aryl, or, for example, methyl, ethyl, propyl, hexyl, octyl, decyl, aryl, cyclohexyl, and the like. a is an number ranging from 0 to 3, b is a number ranging from 0 to 3, a+b is a number ranging from 1 to 3, x is a number from 0 to 3, y is a number from 0 to 3 and the sum of x+y is 3, and wherein $R^E$ is a carboxylic ester containing radical. Typical $R^E$ radicals are those wherein the ester group is formed of one or more fatty acid moieities (e.g. of about 6, often about 6 to 30 carbon atoms) and one or more aliphatic alcohol moieities (e.g. of about 10 to 30 carbon atoms). Examples of such acid moieities include those derived from branched-chain fatty acids such as isostearic, or straight chain fatty acids such as behenic. Examples of suitable alcohol moieties include those derived from monohydric or polyhydric alcohols, e.g. normal alkanols such as n-propanol and branched-chain etheralkanols such as (3,3,3-trimethylolpropoxypropane. Typically, the ester subgroup (i.e. the group containing the carboxylic ester) will be linked to the silicon atom by a divalent aliphatic chain that is at least 2 or 3 carbon atoms in length, e.g. an alkylene group or a divalent alkyl ether group. Most typically, that chain will be part of the alcohol moiety, not the acid moiety. More typically, the cross-linked silicone ester can be a liquid or solid at room temperature. The compound may have a waxy feel and a molecular weight of no more than about 100,000 daltons.

Such silicone resins having the above formula are disclosed in U.S. Pat. Nos. 4,725,658 and 5,334,737, which are hereby incorporated by reference. These ingredients are commercially available from General Electric under the tradenames SF 1318 and SF 1312, respectively.

Pigments and powder may be added as a auxiliary ingredient at a concentration of about 0.001-35%, typically 0.01-20%, more typically 0.1-10%, by weight based the total weight of the composition. Typically the pigments and powders have a particle size of 0.02 to 200 microns, typically 0.5 to 100 microns. The particulate matter may be colored or non-colored (for example white). Suitable powders include bismuth oxychloride, titanated mica, fumed silica, spherical silica, polymethylmethacrylate, micronized teflon, boron nitride, acrylate copolymers, aluminum silicate, aluminum starch octenylsuccinate, bentonite, calcium silicate, cellulose, chalk, corn starch, diatomaceous earth, fuller's earth, glyceryl starch, hectorite, hydrated silica, kaolin, magnesium aluminum silicate, magnesium trisilicate, maltodextrin, montmorillonite, microcrystalline cellulose, rice starch, silica, talc, mica, titanium dioxide, zinc laurate, zinc myristate, zinc rosinate, alumina, attapulgite, calcium carbonate, calcium silicate, dextran, kaolin, nylon, silica silylate, silk powder, sericite, soy flour, tin oxide, titanium hydroxide, trimagnesium phosphate, walnut shell powder, or mixtures thereof. The above mentioned powders may be surface treated with lecithin, amino acids, mineral oil, silicone oil or various other agents either alone or in combination, which coat the powder surface and render the particles more lipophilic in nature.

The powder component also may comprise various organic and inorganic pigments. The organic pigments are generally various aromatic types including azo, indigoid, triphenylmethane, anthraquinone, and xanthine dyes which are designated as D&C and FD&C blues, browns, greens, oranges, reds, yellows, etc. Organic pigments generally consist of insoluble metallic salts of certified color additives, referred to as the Lakes. Inorganic pigments include iron oxides, ultramarines, chromium, chromium hydroxide colors, and mixtures thereof.

The auxiliary ingredient may contain a mixture of both pigmented and non-pigmented powders. The percentage of pigments used in the powder component will depend on the type of cosmetic being formulated.

The auxiliary ingredient of the disclosure may contain 0.001-20%, typically 0.01-10%, more typically 0.05-8% of one or more sunscreens. A sunscreen is defined as an ingredient that absorbs at least 85 percent of the light in the UV range at wavelengths from 290 to 320 nanometers, but transmits UV light at wavelengths longer than 320 nanometers. Sunscreens generally work in one of two ways. Particulate materials, such as zinc oxide or titanium dioxide, as mentioned above, physically block ultraviolet radiation. Chemical sunscreens, on the other hand, operate by chemically reacting upon exposure to UV radiation. Suitable sunscreens that may be included in the compositions of the invention are set forth on page 582 of the CTFA Cosmetic Ingredient Handbook, Second Edition, 1992, as well as U.S. Pat. No. 5,620,965, both of which are hereby incorporated by reference. Examples of such sunscreen materials are p-aminobenzoic acid (PABA), cinoxate, diethanolamine p-methoxycinnamate (DEA-methoxycinnamate), Digalloyl trioleate, dioxybenzone (Benzophenone-8), ethyl 4-[bis-(hydroxypropyl)]aminobenzoate(ethyl dihydroxypropyl PABA), 2-ethythexyl-2-cyano-3,3-diphenylacrylate(octocrylene), ethylhexyl p-methoxycinnamate(Octyl methoxycinnamate), 2-ethylhexyl salicylate (Octyl salicylate), glyceryl aminobenzoate (Glyceryl PABA), homosalate, lawsone with dihydroxyacetone, menthyl anthranilate, oxybenzone (Benzophenone-3), Padimate A (Pentyl Dimethyl PABA), (Octyl Dimethyl PABA), 2-Phenylbenzimidazole-5-sulfonic acid (Phenylbenzimidazole Sulfonic acid), Red Petrolatum, Sulisobenzone (Benzophenone-4), triethanolamine salicylate (TEA-Salicylates), benzophenones, bornelone, butyl PABA, cinnamidopropyl trimethyl ammonium chloride, disodium distryrylbiphenyl disulfonate, PABA, potassium methoxycinnamate, butyl methoxydibenzoylmethane, octyl methoxycinnamate, oxybenzone, octocrylene, octyl salicylate, phenylbenzimidazole sulfonic acid, ethyl hydroxypropyl aminobenzoate, menthyl anthranilate, aminobenzoic acid, cinoxate, diethanolamine methoxycinnamate, glyceryl aminobenzoate, titanium dioxide, zinc oxide, oxybenzone, Padimate O, and mixtures thereof.

The auxiliary ingredient may include about 0.0001-8%, typically 0.001-6%, more typically 0.005-5% by weight of a preservative based on the total weight of the composition. A variety of preservatives are suitable, including such as benzoic acid, benzyl alcohol, ethanol, polyvinyl alcohol, phenoxyethanol, methyl paraben, propyl paraben, benzylhemiformal, benzylparaben, 5-bromo-5-nitro-1,3-dioxane, 2-bromo-2-nitropropane-1,3-diol, butyl paraben, calcium benzoate, calcium propionate, captan, chlorhexidine diacetate, chlorhexidine digluconate, chlorhexidine dihydrochloride, chloroacetamide, chlorobutanol, p-chloro-m-cresol, chlorophene, chlorothymol, chloroxylenol, m-cresol, o-cresol, DEDM Hydantoin, DEDM Hydantoin dilaurate, dehydroacetic acid, diazolidinyl urea, dibromopropamidine diisethionate, DMDM Hydantoin, and all of those disclosed on pages 570 to 571 of the CTFA Cosmetic Ingredient Handbook, Second Edition, 1992, which is hereby incorporated by reference. The auxiliary ingredient may include mixtures of these preservatives.

The auxiliary ingredient of the disclosure may contain vitamins and/or coenzymes, as well as antioxidants. These may be added at a concentration of about 0.001-10%, typically 0.01-8%, more typically 0.05-5% by weight based on the total weight of the composition. Suitable vitamins include the B vitamins such as thiamine, riboflavin, pyridoxin, and so on, as well as coenzymes such as thiamine pyrophoshate, flavin adenin dinucleotide, folic acid, pyridoxal phosphate, tetrahydrofolic acid, and so on. Also Vitamin A and derivatives thereof are suitable. Examples are Vitamin A palmitate, acetate, or other esters thereof, as well as Vitamin A in the form of beta carotene. Also suitable is Vitamin E and derivatives thereof such as Vitamin E acetate, nicotinate, or other esters thereof. In addition, Vitamins D and K are suitable.

Suitable antioxidants are ingredients which assist in preventing or retarding spoilage. Examples of antioxidants suitable for use in the compositions of the invention are potassium sulfite, sodium bisulfite, sodium erythrobate, sodium metabisulfite, sodium sulfite, propyl gallate, cysteine hydrochloride, butylated hydroxytoluene, butylated hydroxyanisole, and mixtures thereof.

The auxiliary ingredient may include one or more alpha or beta hydroxy acids or alpha ketoacids. Typical ranges are 0.01-20%, more typically 0.1-15%, and even more typical 0.5-10% by weight based on the total composition. Suitable alpha hydroxy acids and alpha ketoacids are disclosed in U.S. Pat. No. 5,091,171, which is hereby incorporated by reference. The general structure of such alpha hydroxy acids may be represented by the following formula:

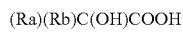

(Ra)(Rb)C(OH)COOH wherein Ra and Rb are H, F, Cl, Br, alkyl, aralkyl, or aryl group of saturated, unsaturated, straight or branched chain or cyclic form having 1-10 carbon atoms, and in addition Ra or Rb may carry OH, CHO, COOH and alkoxy groups having 1 to 9 carbon atoms.

The alpha hydroxy acids may exist in the keto acid form, or the ester form. Examples of such alpha hydroxy acids include glycolic acid, malic acid, pyruvic acid, mandelic acid, lactic acid, methyllactic acid, and mixtures thereof.

Also beta hydroxy acids such as salicylic acid, and derivatives thereof may be included in the compositions of the disclosure. In addition, mixtures of the above alpha and beta hydroxyl acids or alpha ketoacids.

Non-limiting examples of antibacterial agents include bacitracin, phenol, benzethonium chloride, erythromycin, neomycin, tetracycline, chlortetracycline and mixtures thereof.

Non-limiting examples of sunscreens include benzophenones, bornelone, butyl paba, cinnamidopropyl trimethyl ammonium chloride, disodium distryrylbiphenyl disulfonate, paba, potassium methoxycinnamate, butyl methoxydibenzoylmethane, octyl methoxycinnamate, oxybenzone, octocrylene, octyl salicylate, phenylbenzimidazole sulfonic acid, ethyl hydroxypropyl aminobenzoate, menthyl anthranilate, aminobenzoic acid, cinoxate, diethanolamine methoxycinnamate, glyceryl aminobenzoate, titanium dioxide, zinc oxide, oxybenzone, Padimate O, red petrolatum, and mixtures thereof.

Non-limiting examples of preservatives include ethanol, polyvinyl alcohol, phenoxyethanol, benzyl alcohol, methyl paraben, propyl paraben and mixtures thereof.

Non-limiting examples of pH adjusting agents includes potassium acetate, sodium carbonate, sodium hydroxide, phosphoric acid, succinic acid, sodium citrate, citric acid, boric acid, lactic acid, sodium hydrogen carbonate and mixtures thereof.

Bleaching agents include, but not limited to, hydrogen peroxide, perborate and persufate salts. EDTA and other aminocarboxylates may be used as sequestering agents. Antidandruff agents such as zinc pyrithione, salicylic acid, climbazole, ketoconazole, sulfur piroctone olamine, selenium sulfide and mixtures thereof may also be used as an auxiliary ingredient.

The following examples are for illustrative purposes only and are not intended to limit the scope of the claims. In the following examples, Lupasol® G-35 is 50% active and Carbopol® aqua CC is 20% active.

Determination of the Amine Number and the Acid Number

The measurement of the Acid and the Amine Value is performed through a common acid-base titration in the presence of a color indicator. The method is based on the European and American Pharmacopoeias and Standard ISO 660.

Specifically, the acid value measures the quantity of free acid functions titratable with NaOH using Phenolphthalein as an indicator (the endpoint is determined by the slight pink color that persists for at least 15 seconds), and is reported as milliequivalent of acid per grams (meq/g) of the acid substance.

Similarly, the amine value measures the quantity of amine functions titratable with HCl using Bromophenol Blue as an indicator (the endpoint is determined by the slight blue color that persists for at least 15 seconds), and is reported as milliequivalent of amine per gram (meq/g) of the polyamine.

General Procedure for Preparing the Composition of the Disclosure

The at least one acid, at least one water-insoluble ingredient and other optional oil-based ingredients are mixed at a temperature of at least 25° C. in a container A. The at least one polyamine, water and other optional ingredients are mixed at a temperature of at least 25° C. in a container B. Next the contents of container B is slowly added to container A with high shear mixing. After all of container B is added, other optional ingredients described above are added while mixing at high shear. Mixing continues until a homogeneous mixture is obtained.

1. Water-Resistant Properties of Disclosed Composition

A. General Test for the Measurement of the Water-Resistance of Disclosed Composition The water-resistance of a surface treated with the disclosed composition can be measured using a Contact Angle Measurement System K-12 manufactured by Kruss (Germany). This instrument allows one to calculate the degree of water-resistance of a solid surface when it was pushed in and pulled out of water by measuring the angle formed by the water-solid interface. The low contact angle denotes a low water-resistance (water spreads on the surface), and the high contact angle denotes a high water-resistance (water beads on the surface).

In this test, a microscope cover glass (Fisher brand 12-542A, 18 cm×18 cm×0.16 mm) was treated with a solution of the disclosed composition (50 g of Isopropanol (IPA)+ 10 g of the disclosed composition) by dipping the cover glass to half of its length into the testing solution and allowing it to dry. The treated cover glass is then mounted on the Kiruss instrument and the Advancing Contact Angle (Wetting Contact Angle)/Receding Contact Angle (De-wetting Contact Angle) measured using the following parameters:

Measuring Speed: 3 mm/min

Max Immersion Depth: 5 mm

Min Immersion Depth: 0 mm

Sensitivity: 0.01 g

B. Measurements of Contact Angle for Mixtures Xontaining Components (a), (b), (c) and (e)

Following the General procedure described in this above, the Contact Angle of the following compositions were measured (n=5) (Table 1-1):

TABLE 1-1

| IPA (%) | Oleic Acid (%) | Lupasol ® G35 (%) | Mineral Oil (%) | Procetyl AWS (%) | Amine #:Acid # | Advancing Contact Angle (°) | Receding Contact Angle (°) |
|---|---|---|---|---|---|---|---|
| 98.08 | 1.04 | 0.38 | 0.5 | — | 1:1 | 92.6 ± 0.6 | 70.7 ± 0.6 |
| 99.87 | 0.10 | 0.016 | 0.008 | — | 1:0.2 | 81.9 ± 1.4 | 65.4 ± 1.7 |
| 88.08 | 1.04 | 0.38 | 0.5 | 10 | 1:1 | 74.0 ± 2.2 | 63.9 ± 0.4 |

The data in Table 1-1 show that when the concentration of the ingredients in the disclosed composition is lowered and the Amine number: Acid number is outside the claimed range, both the Advancing Contact Angle and the Receding Contact Angle decrease to below 66 degrees. A decrease in the contact angle can also be seen in a case where additional ingredients such as nonionic surfactant (Procetyl AWS) are added to the claimed composition. These results demonstrate that not all compositions necessarily have the disclosed contact angle of 66 degrees.

Table 1-2 lists the contact angles on an untreated and a disclosed composition treated glass surface (n=10):

TABLE 1-2

Tested Disclosed Compositions

| Isostearic Acid (%) | Lupasol ® G35 (%) | Ratio of amine number to acid number | Min. Oil (%) | Water (%) | IPA (%) | Contact Angle (°) Advancing | Receding |
|---|---|---|---|---|---|---|---|
| | | | | | 100 | 9.8 ± 2.9 | 6.7 ± 1.6 |
| 0.3 | 0.13 | 1:0.84 | 0.1 | 16.47 | 83.0 | 69.1 ± 1.0 | 66.4 ± 0.3 |
| 1.5 | 0.13 | 1:4.19 | 0.1 | 15.27 | 83.0 | 91.5 ± 1.1 | 73.4 ± 1.8 |
| 5.0 | 1.0 | 1:1.81 | 2.0 | 9.0 | 83.0 | 94.4 ± 1.0 | 73.5 ± 0.6 |

The data demonstrate a significant increase in water-resistance of the glass surface upon treating with the disclosed composition as evidenced by the increase in both the Advancing Contact Angle and the Receding Contact Angle.

C. Water-Resistance of Hair Treated with the Disclosed Composition

Bleached hair (from IHIP, New York) was treated with various shampoo formulas containing the disclosed composition six times (1 g shampoo/g hair, 1 cycle=1 minute shampoo, 30 second rinse). The contact angles between water and the single hair fiber (n=12) were measured. The results are shown in the following Table (Table 1-3):

The data shows that hair shampooed with the disclosed composition containing shampoo is water-proof as indicated by the increase in the Receding Contact Angle.

2. Studies on Non-Transfer of Pigments using the Disclosed Composition.

A. Study on Non-Transfer of Pigments in the Disclosed Composition

An aqueous formula of the disclosed composition containing a pigment (Red 7) was applied onto hair. The hair was blotted with tissue sheets and then the sheets were read with a spectrophotometer to measure the L value and the a value.

The L value is a measure of lightness/darkness. A lower L value indicates that the color is darker and a higher L value indicates the color is lighter. The a value is a measure of redness. A lower a value indicates less redness and a higher a value indicates more redness. In this study, the transfer of pigment onto the white sheet of tissue paper is indicated by a lower L value (darker) and a higher a value (redder).

Materials:

Hair: Regular Bleached hair, 5 inches long (excluding the glue strip), 1 cm wide (at glue strip), 5 swatches per treatment type.

TABLE 1-3

Shampoo Containing Disclosed Composition (qs with water)

| SLES[1] (%) | Cocamidopropyl Betaine (%) | Fatty Acid (%) | Polyamine (%) | Water-Insoluble Ingredients (%) | Ratio of Amine # to Acid # | Contact Angle (°) Advancing | Receding |
|---|---|---|---|---|---|---|---|
| 7 | 3 | — | — | — | — | 65.61 ± 4.83 | 0.04 ± 0.12 |
| 7 | 3 | Isostearic Acid (0.5) | Lupasol ® G35 (0.4) | Min Oil (0.5) | 1:0.91 | 60.39 ± 2.91 | 38.60 ± 4.53 |
| 7 | 3 | Oleic Acid (0.5) | Carbopol ® aqua CC (0.75) | Min Oil (1.0) | 1:1.05 | 55.06 ± 3.77 | 12.84 ± 11.02 |
| 7 | 3 | Oleic Acid (2.5) | Carbopol ® aqua CC (0.75) | Dow Corning ® 200 Fluid 60K (0.75) | 1:5.24 | 58.48 ± 3.94 | 35.10 ± 7.43 |

[1] sodium laureth sulfate

Test Treatment: Disclosed composition consisting of: Lupasol® G35 8.29%, Oleic Acid 20.71%, Isododecane 30%, and Red 7 10%, in DI Water (ratio of amine number to acid number is 1:0.92).

Control Treatment: Traditional Soap formula consisting of: DI Water 34.74%, MEA (Monoethanolamine) 4.55%, Oleic Acid 20.71%, Isododecane 30%, Red 7 10%

Konica Minolta® Spectrophotometer

Kimwipe® Tissue Paper (Large)

Procedure:

First, using the spectrophotometer, take baseline reading of the kimwipe tissue paper. Next, apply treatments, (0.5 g per gram of hair) and massage in for a minute. Air dry by hanging for 20 minutes. Place the treated hair between two sheets of kimwipes and place 3.5 kg weight on top for 1 minute. Measure L and a values of surfaces of kimwipes where the swatches were pressed. Calculate averages and % changes.

Results:

The hair treated with the disclosed composition had significantly less pigment transfer, by t-test, indicated by lower % change of L value and lower % change of a value (Table 2-1). The hair treated with the Traditional soap had significantly more pigment transfer, by t-test, indicated by higher % change of L value and higher % change of a value.

TABLE 2-1

|  | % change of L value | % change of a value |
| --- | --- | --- |
| Traditional soap | 37.44% | 6510.19% |
| Disclosed Composition | 10.29% | 1646.71% |

Conclusion:

The hair treated with disclosed composition had significantly less pigment transfer than the traditional soap treated swatches.

B. Non-Transfer of Pigment Study of The Disclosed Composition (Anhydrous)

Objective:

An anhydrous formula of the disclosed composition containing a pigment (Red 7) were applied onto hair. The hair was blotted with tissue sheets and then the sheets were read with a spectrophotometer to measure the L value and the a value.

The L value is a measure of lightness/darkness. A lower L value indicates that the color is darker and a higher L value indicates the color is lighter. The a value is a measure of redness. A lower a value indicates less redness and a higher a value indicates more redness. In this study, the transfer of pigment onto the white sheet of tissue paper is indicated by a lower L value (darker) and a higher a value (redder).

Materials:

Hair: Regular Bleached hair, 5 inches long (excluding the glue strip), 1 cm wide (at glue strip), 5 swatches per treatment type.

Test Treatment: Disclosed composition consisting of: Isopropanol 54.5%, Carbopol® Aqua CC 15.5%, Isostearic Acid 10%, Dow Corning® 556 10%, Red 7 10% (the ratio of amine number to acid number is 1:1)

Control Treatment: Traditional Soap formula consisting of: Isopropanol 67.83%, MEA (Monoethanolamine) 67.83%, Isostearic Acid 10%, Dow Corning® 556 10%, Red 7 10%

Konica Minolta® Spectrophotometer

Kimwipe® Tissue Paper (large)

Procedure:

First, using the spectrophotometer, take baseline reading of kimwipe, next, apply treatments, (0.5 g per gram of hair) and massage in for a minute. Air dry by hanging for 20 minutes. Place the treated hair between two sheets of kimwipes and place 3.5 kg weight on top for 1 minute. Measure L and a values of surfaces of kimwipes where the swatches were pressed. Calculate averages and % changes.

Results:

The hair treated with the disclosed composition had significantly less pigment transfer, by t-test, indicated by lower % change of L value and lower % change of a value (Table 2-2). The hair treated with the anhydrous Traditional soap had significantly more pigment transfer, by t-test, indicated by higher % change of L value and higher % change of a value.

TABLE 2-2

|  | % change of L value | % change of a value |
| --- | --- | --- |
| Traditional soap | 39.75% | 4810.93% |
| Disclosed Composition | 7.38% | 605.95% |

Conclusion:

The hair treated with the disclosed composition had significantly less pigment transfer than the traditional soap treated swatches.

3. Non-Transfer of Oil Studies with the Disclosed Composition.

A. Non-Transfer of Oil Study with the Disclosed Composition

An aqueous formula of the disclosed composition containing mineral oil was applied on the hair. The hair was blotted with oil blotting sheets and then the sheets were read with a spectrophotometer to measure the L value.

Background:

The L value is a measure of lightness/darkness. A lower L value indicates that the color is darker and a higher L value indicates the color is lighter. In this study, oil that transfers onto the blotting sheet with a black background will appear dark on the sheets, as indicated by lower L values.

Materials:

Hair: Regular Bleached hair, 5 in long (excluding the glue strip), 1 in wide (at glue strip), 5 swatches per treatment type.

Test Treatment: Disclosed composition formula consisting of: Isododecane 24.5%, Carbopol® Aqua CC 15.5%, Isostearic Acid 10%, and Mineral Oil 10% in DI Water (the ratio of the amine number to the acid number is 1:1)

Control Treatment: Traditional Soap formula consisting of: DI Water 40%, Isododecane 37.83%, MEA 2.17%, Isostearic Acid 10%, Mineral Oil 10%

Konica Minolta® Spectrophotometer

Blow Dryer

Johnson and Johnson Clean and Clear® Oil Blotting Sheets

Procedure:

First, using the spectrophotometer, take baseline reading of the oil blotting sheets. Next, apply treatments, (0.5 g per gram of hair) and massage in for a minute. Blow-dry the swatches at 55° C. for 15 minutes. Place the treated hair between two oil blotting sheets and place 3.5 kg weight on top for 1 minute. Place the two blotting sheets on a black surface and measure L and a values of surfaces where the swatches were pressed. Calculate averages and % changes.

Results:

The swatches treated with the disclosed composition had significant less transfer of oil, by t-test, indicated by low percent change of L value (Table 3-1). The swatches treated with the aqueous traditional soap had significant amount of oil transfer, by t-test, indicated by high percent change of L value.

TABLE 3-1

| | % change of L value |
|---|---|
| Traditional soap | 8.93% |
| Disclosed Composition | 0.56% |

Conclusion:

The hair treated with the disclosed composition had significantly less transfer of oil than the hair treated with an aqueous formula of traditional soap.

B. Non-Transfer of Oil Study with the Disclosed Composition (Anhydrous)

An anhydrous formula of the disclosed composition containing mineral oil was applied on the hair. The hair was blotted with oil blotting sheets and then the sheets were read with a spectrophotometer to measure the L value.

Background:

The L value is a measure of lightness/darkness. A lower L value indicates that the color is darker and a higher L value indicates the color is lighter. In this study, oil that transfers onto the blotting sheet with a black background will appear dark on the sheets, as indicated by lower L values.

Materials:

Hair: Regular Bleached hair, 5 in long (excluding the glue strip), 1 in wide (at glue strip), 5 swatches per treatment type.

Test Treatment: Disclosed composition consisting of: Isopropanol 66.2%, Lupasol® G35 5.7%, Oleic Acid 14.3%, Mineral Oil 14.3%

Control Treatment: Traditional Soap formula consisting of: Isopropanol 68.8%, MEA 3.1%, Oleic Acid 14.3%, Mineral Oil 14.3% (the ratio of amine number to acid number is 1:0.92)

Konica Minolta® Spectrophotometer

Blow Dryer, comb

Procedure:

First, using the spectrophotometer, take baseline reading of the oil blotting sheets. Next, apply treatments, (0.5 g per gram of hair) and massage in for a minute. Blow-dry the swatches at 55° C. for 15 minutes. Place the treated hair between two oil blotting sheets and place 3.5 kg weight on top for 1 minute. Place the two blotting sheets on a black surface and measure L and a values of surfaces where the swatches were pressed. Calculate averages and % changes.

Results:

The swatches treated with the disclosed composition had significantly less transfer of oil, by t-test, indicated by low percent change of L value (Table 3-2). The swatches treated with the anhydrous traditional soap had significant amount of oil transfer, by t-test, indicated by high percent change of L value.

TABLE 3-2

| | % change of L value |
|---|---|
| Traditional soap | 26.02% |
| Disclosed Composition | 1.42% |

Conclusion:

The hair treated with the anhydrous formula of the disclosed composition had significantly less transfer of oil than the hair treated with an anhydrous formula of traditional soap.

Overall the results from experiments 1-3 illustrated the ability of the disclosed composition to unexpectedly improve the properties of keratinous substrates. Specifically the disclosed composition unexpectedly improves keratinous properties such as water-resistance, non-transfer of pigment and oil.

The exact formulation that provides the unexpected benefits varies with the specific application. Some non-limiting applications and typical fatty acid and polyamine contents for each application are given in Table A.

TABLE A

Typical Fatty Acid, Polyamine and Water Insoluble Ingredient Contents (wt %) for Various Applications

| | Wt % fatty Acid | % Polyamine | Ratio of Amine Number to Acid Number | Water insoluble ingredient |
|---|---|---|---|---|
| Shampoo | 1.25-5.0 | 0.1-0.4 | 1:1-1:10 | 0.05-0.2 |
| Conditioner | 0.5-2 | 0.06-0.25 | 1:1-1:6 | 0.5-2 |
| Styler | 2.5-10 | 0.03-0.13 | 1:3-1:20 | 2.0-9.0 |
| Tamer | 4.0-16 | 0.3-1.5 | 1:1-1:5 | 6.0-26.0 |
| Curl Definer | 3.5-14 | 0.12-0.5 | 1:1-1:15 | 6.0-25.0 |
| Finishing Cream | 4.5-18 | 0.12-0.5 | 1:1-1:20 | 2.0-8.0 |

The foregoing description illustrates and describes the present disclosure. Additionally, the disclosure shows and describes only the preferred embodiments of the disclosure, but, as mentioned above, it is to be understood that it is capable of changes or modifications within the scope of the concept as expressed herein, commensurate with the above teachings and/or skill or knowledge of the relevant art. The embodiments described hereinabove are further intended to explain best modes known of practicing the invention and to enable others skilled in the art to utilize the disclosure in such, or other, embodiments and with the various modification required by the particular applications or uses disclosed herein. Accordingly, the description is not intended to limit the invention to the form disclosed herein. Also, it is intended that the appended claims be construed to include alternative embodiments.

All publications, patents and patent applications cited in this specification are herein incorporated by reference, and for any and all purposes, as if each individual publication, patent or patent application were specifically and individually indicated to be incorporated by reference. In the case of inconsistencies, the present disclosure will prevail.

What is claimed:

1. A composition comprising
    (a) at least one polyamine selected from the group consisting of a polyethyleneimine, an amine substituted polyacrylate crosspolymer, an amine substituted polyacrylate, an amine substituted polymethacrylate, and mixtures thereof,
    (b) at least one acid selected from the group consisting of capric acid, caprylic acid, isosteric acid, oleic acid, stearic acid, lauric acid, linoleic acid, linolenic acid, laureth-5 carboxylic acid, laureth-11 carboxylic acid, and mixtures thereof,
    (c) at least one water-insoluble ingredient selected from the group consisting of an oil and isododecane, and
    (d) solvent,
    wherein
    the ratio of the amine groups in the at least one polyamine to the acid groups in the at least one acid is from about 1:1 to about 1:10,
    the composition has a receding contact angle of at least 66 degrees on glass, and
    the composition is not a shampoo.

2. The composition as claimed in claim 1, wherein the at least one polyamine (a) is a polyethyleneimine or an amine substituted polyacrylate crosspolymer.

3. The composition as claimed in claim 1, wherein the at least one water-insoluble ingredient (c) is isododecane.

4. The composition as claimed in claim 1, wherein the at least one polyamine (a) is present in a positive amount up to about 30% by weight, based on the weight of the composition.

5. The composition as claimed in claim 1, wherein the at least one acid (b) is present in a positive amount up to about 50% by weight, based on the weight of the composition.

6. The composition as claimed in claim 1, wherein the at least one water-insoluble ingredient (c) is present in a positive amount up to about 50% by weight, based on the weight of the composition.

7. The composition as claimed in claim 1, wherein solvent (d) is present in an amount of from about 10% to about 90% by weight, based on the weight of the composition.

8. A composition comprising:
   (a) a positive amount up to 30% by weight of a polyethyleneimine;
   (b) a positive amount up to 50% by weight of at least one acid selected from the group consisting of capric acid, caprylic acid, isosteric acid, oleic acid, stearic acid, lauric acid, linoleic acid, linolenic acid, laureth-5 carboxylic acid, laureth-11 carboxylic acid, and mixtures thereof;
   (c) a positive amount up to 50% by weight of an oil and/or isododecane, and
   (d) 10% to 90% by weight of solvent;
     wherein the ratio of the amine groups in the polyethyleneimine to the acid groups in the fatty carboxylic acid is from 1:1 to 1:10, and wherein the composition has a receding contact angle of at least 66 degrees on glass.

9. The composition as claimed in claim 8, wherein the fatty carboxylic acid is selected from the group consisting of isosteric acid and oleic acid.

10. The composition as claimed in claim 9, wherein the ratio of the amine groups in the polyethyleneimine to the acid groups is about 1:1.

11. The composition as claimed in claim 1, further comprising at least one auxiliary ingredient (e), wherein the at least one auxiliary ingredient is selected from the group consisting of an amino acid, a protein, a cationic conditioner, a cationic polymer, a anionic surfactant, a nonionic surfactant, an amphoteric surfactant, a zwitterionic surfactant, a viscosity modifier, an organosiloxane polymer, a wax, a silicone resin, a pigment, a powder, a preservative, an antioxidant, a vitamin, an alpha hydroxy acid, a beta hydroxy acid, an alpha keto acid, an antibacterial agent, a sunscreen, a preservative, a pH adjusting agent, a bleaching agent, a perfume, a sequestering agent, an anti-dandruff agent and mixtures thereof.

12. A method of treating a keratinous substrate comprising contacting the keratinous substrate with a composition according to claim 1.

13. The method as claimed in claim 12, wherein the keratinous substrate is at least one selected from the group consisting of hair, skin, lips, nails and eyelashes.

14. The composition as claimed in claim 11, wherein the at least one auxiliary ingredient (e) is present in a positive amount up to about 50%, based on the weight of the composition.

* * * * *